(12) United States Patent
Heil et al.

(10) Patent No.: US 9,002,441 B2
(45) Date of Patent: Apr. 7, 2015

(54) ELECTRONIC FETAL MONITORING APPLICATIONS AND DISPLAY

(75) Inventors: Christopher Heil, Liberty, MO (US);
Jeremy Flores, Overland Park, KS (US);
Carol George, Spring Hill, KS (US)

(73) Assignee: Cerner Innovation, Inc., Kansas City, KS (US)

(*) Notice: Subject to any disclaimer, the term of this patent is extended or adjusted under 35 U.S.C. 154(b) by 560 days.

(21) Appl. No.: 12/564,569

(22) Filed: Sep. 22, 2009

(65) Prior Publication Data
US 2011/0071414 A1   Mar. 24, 2011

(51) Int. Cl.
| A61B 5/04 | (2006.01) |
| A61B 5/0444 | (2006.01) |
| A61B 5/00 | (2006.01) |

(52) U.S. Cl.
CPC ............ *A61B 5/0444* (2013.01); *A61B 5/0011* (2013.01); *A61B 5/411* (2013.01); *A61B 5/4362* (2013.01)

(58) Field of Classification Search
CPC ............ A61B 5/0006; A61B 5/02405; A61B 5/02411; A61B 5/033; A61B 5/0444; A61B 5/4356; A61B 5/4343; A61B 5/435; A61B 5/0011; A61B 5/024

USPC .............................. 600/511, 595, 509; 607/32
See application file for complete search history.

(56) References Cited

U.S. PATENT DOCUMENTS

| 5,442,940 | A | * | 8/1995 | Secker et al. ................. 600/483 |
| 5,724,985 | A | * | 3/1998 | Snell et al. ..................... 600/510 |
| 5,785,660 | A | * | 7/1998 | van Lake et al. .............. 600/523 |
| 7,412,283 | B2 | * | 8/2008 | Ginzburg et al. ............. 600/517 |
| 2003/0208128 | A1 | * | 11/2003 | Hamilton et al. ............. 600/509 |
| 2004/0054295 | A1 | * | 3/2004 | Ramseth ....................... 600/509 |
| 2004/0197727 | A1 | * | 10/2004 | Sachdeva et al. ............... 433/24 |
| 2006/0265020 | A1 | * | 11/2006 | Fischell et al. .................. 607/30 |
| 2008/0154155 | A1 | * | 6/2008 | Nishihara et al. ............. 600/595 |
| 2009/0240158 | A1 | * | 9/2009 | Hamilton et al. ............. 600/511 |
| 2011/0282225 | A1 | * | 11/2011 | Anderson et al. ............. 600/510 |

* cited by examiner

*Primary Examiner* — Niketa Patel
*Assistant Examiner* — William Levicky
(74) *Attorney, Agent, or Firm* — Shook, Hardy & Bacon L.L.P

(57) ABSTRACT

Systems, methods, and computer-readable media for managing healthcare environments are provided. In embodiments, a first waveform tracing for data received from one or more medical devices for a first individual is displayed. A second waveform tracing for data received from one or more medical devices for a second individual is displayed. In response to the determination to hide the first waveform tracing, only displaying the second waveform tracing.

6 Claims, 15 Drawing Sheets

US 9,002,441 B2

ELECTRONIC FETAL MONITORING APPLICATIONS AND DISPLAY

BACKGROUND

Electronic fetal monitoring (EFM) is the use of electronic fetal heart-rate monitoring for the evaluation of fetal well-being. EFM devices are used during pregnancy, labor and birth in over 99% of patients. Clinicians base clinical decisions utilizing the waveform information produced by EFM devices. EFM devices may show fetal heart rate deceleration and acceleration patterns that are monitored by clinicians. Additional information such as heart rate, blood pressure and uterine pressure and contraction information may also be monitored. This information maybe used by clinicians to determine if a fetus is healthy or if medical intervention, such as delivery by surgical operation, is necessary.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to methods, systems and computer storage media having computer-executable instructions embodied thereon that, when executed, cause a computing device to perform a method of displaying waveform tracings for data received from one or more medical devices. A first waveform tracing for data received from one or more medical devices for a first individual is displayed. A second waveform tracing for data received from one or more medical devices for a second individual is displayed. In response to the determination to hide the first waveform tracing, only displaying second waveform tracing.

Embodiments of the present invention relate to methods, systems and computer storage media having computer-executable instructions embodied thereon that, when executed, cause a computing device to perform a method of displaying on a user device alarm-triggering events detected by the medical device based on the location of the user device. Patient data which triggers an alarm is received from a medical device. The physical location of first and second user display devices is determined. The physical location of the first and second user display devices is independent from the users logged onto the first and second user display devices. It is determined that the physical location of the first user display device is designated to have the alarm displayed. It is determined that the physical location of the second user display device is not designated to have the alarm displayed. In response to the determinations, the content of the alarm is displayed on the first user display device and not the second user display device.

Embodiments of the present invention relate to methods, systems and computer storage media having computer-executable instructions embodied thereon that, when executed, cause a computing device to perform a method of displaying medical annotations for a patient. A first medical annotation for a patient relating to one or more of the patient's demographic information, medical condition, or status is received from a clinician. A request not to display the first annotation when annotations are displayed for the patient is received. The first annotation for the patient and the request to hide the first annotation are stored in the patient's electronic medical record. Additional medical annotations are received and stored for the patient. A request from to view medical annotations for the patient is received. The stored first annotation and additional annotations are accessed for the patient. It is determined that the first annotation has been requested not to be displayed. In response to the determination, the additional patient annotations are displayed but the first annotation for the patient is not.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
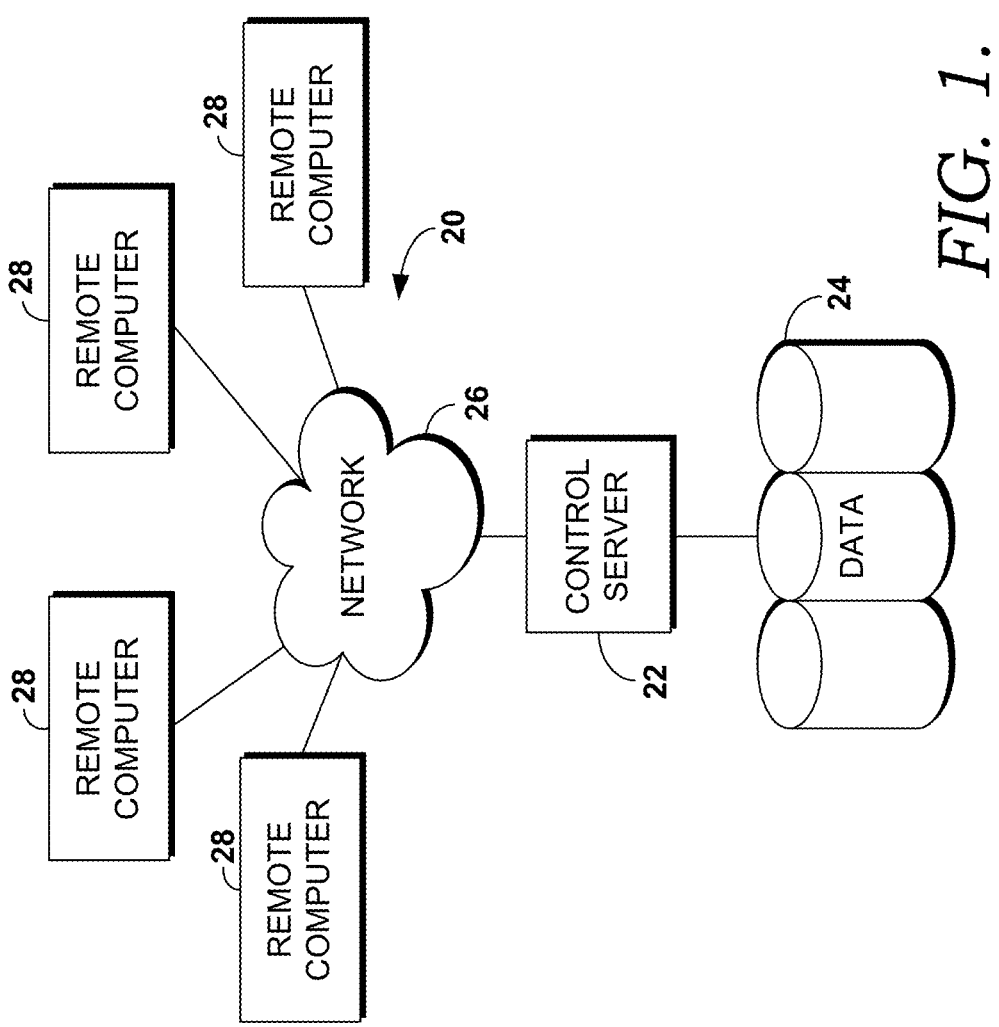
FIG. 1 is a block diagram of an exemplary computing environment suitable for use in implementing embodiments of the present invention.

Referring to the drawings in general, and initially to FIG. 1 in particular, an exemplary computing system environment, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22. The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Fetal monitoring module 210 may reside on one or more computing devices, such as, for example, computing device 22 described above with reference to FIG. 1. By way of example only and not limitation, computing devices may be a server, personal computer, desktop computer, laptop computer, handheld device, mobile handset, consumer electronic device, or the like. It should be noted, however, that embodiments are not limited to implementation on such computing devices, but may be implemented on any a variety of different types of computing devices within the scope of embodiments thereof.

Figure 2:
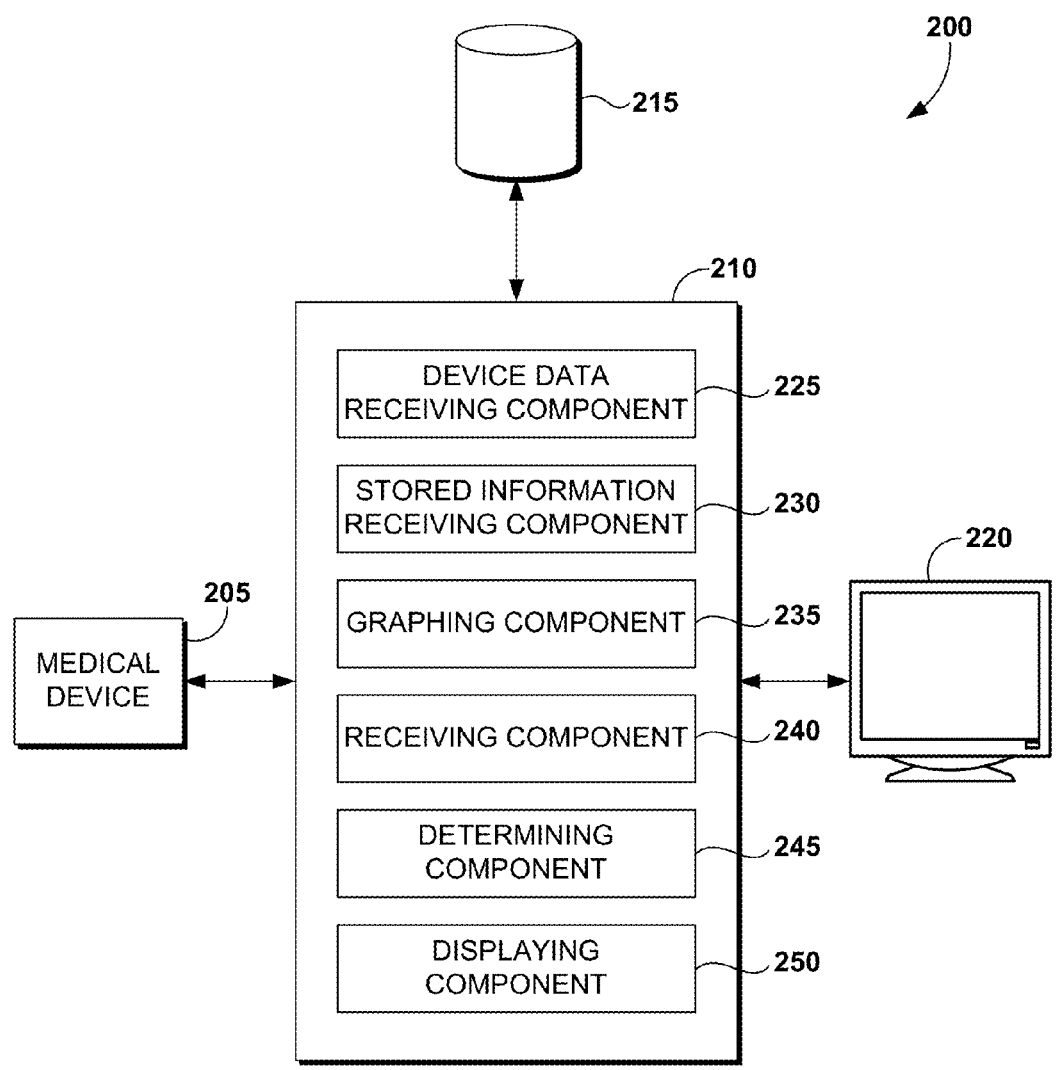
FIG. 2 is an exemplary system architecture suitable for use in implementing embodiments of the present invention.

As previously set forth, embodiments of the present invention related to computing systems for monitoring and displaying information regarding the health of mother and baby during pregnancy, labor and delivery. With reference to FIG. 2, a block diagram is illustrated that shows an exemplary computing system architecture for displaying and monitoring information during pregnancy, labor and delivery. It will be appreciated that the computing system architecture shown in FIG. 2 is merely an example of one suitable computing system and is not intended as having any dependency or requirement related to any single module/component or combination of modules/components.

The computing system includes one or more medical devices 205, fetal monitoring module 210, database 215 and graphical display 220. Discrete data elements are received from device 205. A medical device 205 may be any device, stationary or otherwise, that may be used to treat a patient in a hospital, doctor's office, etc. For exemplary purposes only and not limitation, medical devices include fetal heart rate monitors, blood pressure monitors, uterine pressure and contraction activity monitors, blood oxygen saturation monitors, maternal heart rate monitors, other monitors, ventilators, pumps (e.g., infusion pumps, balloon pumps), a patient's bed, sequential compression devices, electronic security devices, and the like.

Database 215 contains a variety of information data for the patient in a patient's electronic medical record (EMR). As utilized herein, the acronym "EMR" is not meant to be limiting, and may broadly refer to any or all aspects of the patient's medical record rendered in a digital format. Generally, the EMR is supported by systems configured to coordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Graphical display device 220 may be a monitor, computer screen, project device or other hardware device for displaying output capable of displaying graphical user interfaces.

Fetal monitoring module 210 receives and displays data from a medical device for mother and baby during pregnancy, labor and delivery. Fetal monitoring module 210 may reside on one or more computing devices, such as, for example, computing device 22 described above with reference to FIG. 1. By way of example, computing device 22 includes a computer processor and may be a server, personal computer, desktop computer, laptop computer, handheld device, mobile handset, consumer electronic device, or the like.

Fetal monitoring module 210 comprises device data receiving component 215, stored information receiving component 230, graphing component 235, receiving component 240, determining component 245 and displaying component 250. Device data receiving component 225, receives discrete data from one or more medical devices 205. It will be appreciated that while fetal monitoring module 210 is depicted as being connected to a single medical device 225, fetal monitoring module 210 may receive discrete data from multiple medical devices including medical devices monitoring both a mother and her unborn baby.

The data received by data receiving component 225 includes device related output from the medical device. For example, data receiving component 225 may receive data from a fetal heart monitor, a maternal heart monitor, maternal blood pressure monitor, ultrasound, fetal scalp electrodes and a uterine pressure monitor. In one embodiment, the patient is continuously monitored and new data points are sent to the data receiving component 225 such that they may be plotted and displayed in a waveform quickly or in real-time.

Stored information receiving component 230 receives information from database 215 including a variety of information data for the patient in a patient's electronic medical record (EMR). By way of example, the EMR may store one or more of the following types of information: annotations regarding a patient's condition; patient demographic; medical history (e.g., examination and progress reports of health and illnesses); medicine and allergy lists/immunization status; laboratory test results, radiology images (e.g., sonogram, X-rays, CTs, MRIs, etc.); evidence-based recommendations for specific medical conditions; a record of appointments and physician's notes; billing records; and data received from an associated medical device.

Graphing component 235 converts the data received from medical device 205 into electronic waveforms that can be displayed as tracings or graphs. The term waveform refers to the shape of a graph of the varying quantity against time. Exemplary electronic waveforms for data from medical devices are shown in FIGS. 6-9. For example, as data comes in indicating a patient's heart rate, it is graphed as function of time in a waveform. In the exemplary waveforms, the newest data is plotted on the right side of the waveform. The prior data points are to the left of the newest plotted point. Exemplary data that is received and may be displayed in waveform includes, but is not limited to, fetal blood oxygenation saturation level, uterine activity, maternal heart rate, maternal EKG data, maternal blood pressure, fetal heart rate (beats per minute) and maternal blood oxygen saturation level. Fetal blood oxygenation saturation level (FapO2%) may include discrete data elements such as oxygenation saturation level, $CO_2$ level, base excess and pH. Uterine activity may include discrete data elements such as uterine pressure and contraction activity of the uterine muscle (mmHG) and may be measured using tocodynamometry to determine progress of labor. Maternal heart rate is captured as beats per minute. Maternal blood pressure discrete data elements include systolic blood pressure (mmHG), diastolic blood pressure (mmHG) and mean arterial pressure (mmHG). Fetal heart rate includes beats per minute and may be captured by a monitor, ultrasound, and fetal scalp electrodes. Maternal blood oxygenation saturation level (SpO2%) may include discrete data elements such as oxygenation saturation level, $CO_2$ level, base excess and pH.

Receiving component 240 receives inputs from a user utilizing a computing device 220 with a processor such as computing device 22 of FIG. 1. Receiving component 240 may receive a variety of inputs. For example, subcomponents of receiving component 240 receive inputs including requests to hide one or more of the waveforms, textual annotations, requests to hide one or more textual annotations, requests to save snapshots of a particular time period of the waveforms and associate the snapshots with other files, requests to view alerts, inputs of patient information and a variety of other inputs. These inputs will be discussed in more detail below. It will be appreciated that receiving component 240 comprises at least one subcomponent and may have any number of subcomponents. Alternatively, one or more subcomponents may be separate receiving components.

Determining component 245 makes a variety of determinations utilizing the input received by receiving component 210 and may have a number of subcomponents. For example, one subcomponent of determining component 245 determines to no longer display a waveform on the graphical user interface if a request to hide the waveform is received. One subcomponent of determining component 245 determines to hide annotations displayed if there has been a request to hide an annotation. Another subcomponent of determining component 245 determines an area of the one or more waveforms that is associated with the time of a selected annotation. It will be appreciated that determining component 245 comprises at least one subcomponent and may have a number of subcomponents. Alternatively, one or more subcomponents may be separate determining components.

Displaying component 250 utilizes a computer processor to display on display device 220 a variety of information. The information displayed regarding the patient's condition may come from medical device 205 and database 215. For example, subcomponents of displaying component 250 display graphical user interfaces including information on patient alerts, number of alerts, waveforms for one or more individuals, patient information and annotations. It will be appreciated that displaying component 250 comprises at least one subcomponent and may have a number of subcomponents. Alternatively, one or more subcomponents may be separate determining components.

Figure 3:
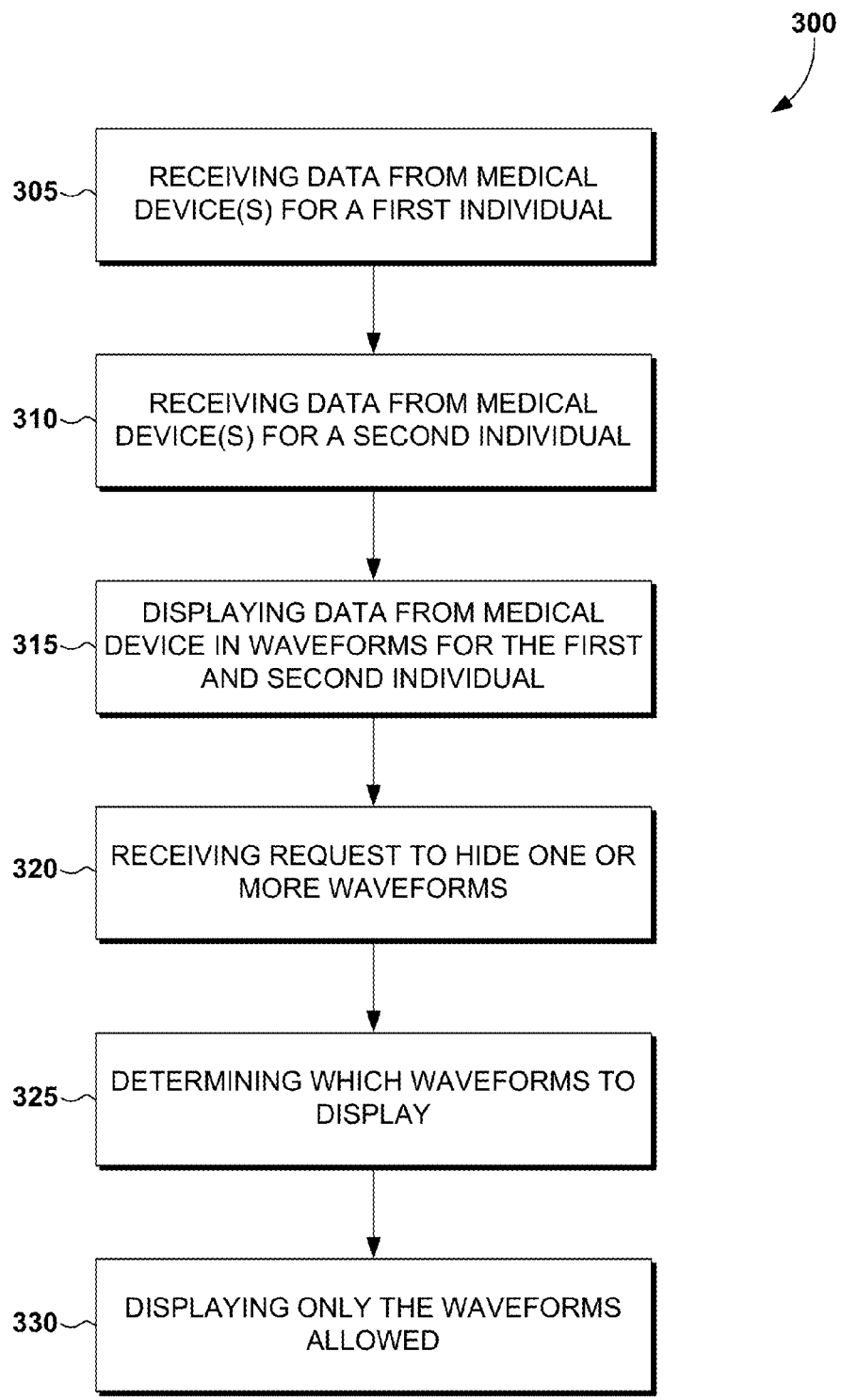
FIG. 3 is an illustrative flow diagram of a method for displaying waveform tracings from a medical device for two individuals, in accordance with an embodiment of the present invention.

Referring next to FIG. 3, a computer-implemented method 300 for determining and displaying only requested medical device waveforms for one or more individuals is shown. Computer-implemented method 300 is performed by one or more computer processors. At step 305, monitoring data from one or more medical devices for a first individual are received. In one embodiment, the first individual is a maternity patient. Exemplary monitoring data for the maternity patient includes heart rate data from a heart rate monitor, uterine pressure and contraction information from a uterine pressure and contraction activity monitor, blood oxygen saturation data from a blood oxygen saturation monitor(s) and blood pressure from a blood pressure monitor(s).

At step 310, monitoring data from one or more medical devices for a second individual is received. In one embodiment, the second individual is the unborn baby of the maternity patient. Exemplary monitoring data for the unborn baby of the maternity patient includes fetal heart rate from a fetal heart rate monitor and fetal blood oxygen saturation data from a blood oxygen saturation monitor. In one embodiment, the first individual may be an unborn baby of a maternity patient and the second individual is a second unborn baby of the same maternity patient.

At step 315, the data from the medical devices for the first and second individuals is displayed as waveform tracings. Graphing component 235 converts the data received from medical device 205 into electronic waveform tracings that can be displayed by displaying component 250 as tracings or graphs. The term waveform refers to the shape of a graph of the varying quantity against time. Exemplary electronic waveforms for data from medical devices are shown in FIGS. 6-9.

At step 320 of FIG. 3, a request to hide one or more of the waveforms displayed is received. In one embodiment, a user, such as a nurse or doctor, may request to hide one or more of the waveforms displayed for a first individual (e.g., patient, maternity patient or unborn baby of maternity patient) and/or second individual (e.g., patient, maternity patient or unborn baby of maternity patient). For example, and as discussed in more detail below, a user may choose to hide a waveform tracing for a maternity patient (e.g., waveform tracing not needed or is interfering with a waveform being displayed for the unborn baby). The request may be a request to hide or alternatively a request to view only certain waveforms.

At step 325, it is determined which waveforms to display based on the request from the user. For example, if the user has requested to view only the waveform of one unborn baby from a group of multiple babies, the determining component 245 would determine to display only the waveform of the one unborn baby and not the waveforms of the other babies. In another example, only the waveform tracing(s) of the maternity patient and not the unborn baby may be selected to be displayed. At step 330, only the waveforms as determined by determining component 245 to be displayed are displayed. Furthermore, it will be appreciated that waveform tracings for more than two babies may be displayed.

Figure 4:
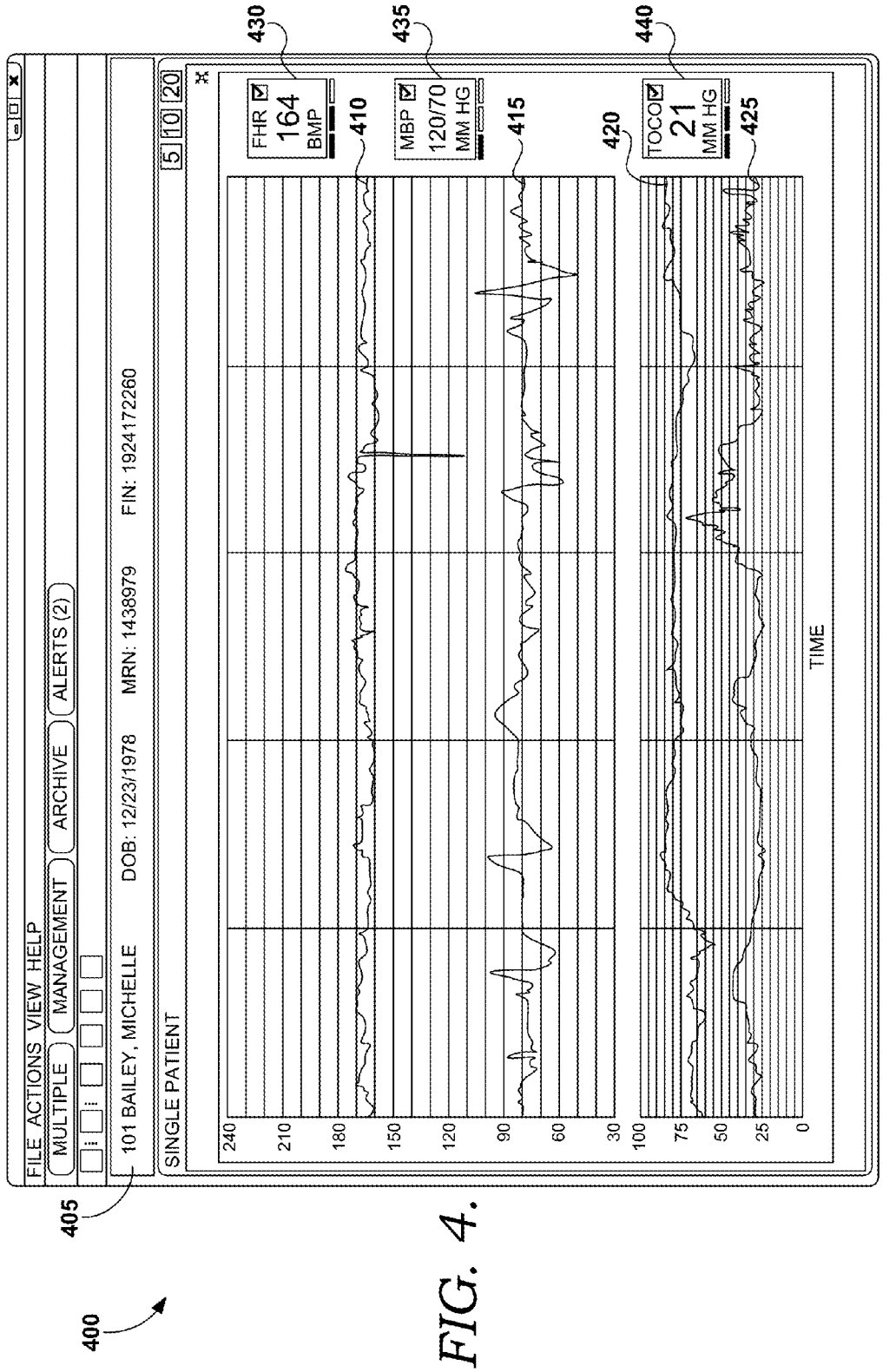
FIG. 4 is an illustrative screen display showing waveform tracings from one or more medical devices, in accordance with an embodiment of the present invention.

With reference to FIG. 4, a graphical user interface embodied on a computer-storage media showing data waveforms from one or more medical devices is shown. Display 400 includes waveform tracings for a single maternity patient 405 and her unborn baby. Waveform tracings for fetal heart rate 410, maternal blood pressure 415, maternal heart rate 420 and tocodynamonetry (TOCO) 425. Maternal blood pressure waveform 435, maternal heart rate waveform 420 and maternal uterine pressure and contraction waveform 425 are displayed for a first individual (maternity patient) along with fetal heart rate waveform 410 for a second individual (unborn baby of maternity patient). Display 400 also includes a display of the most recent numerical value of the data received from medical devices. Numerical measurements for patient 405 and her unborn baby for fetal heart rate 430 maternal blood pressure 435 and TOCO 440 are displayed on the graphical user interface along with the waveform of the data.

Figure 5:
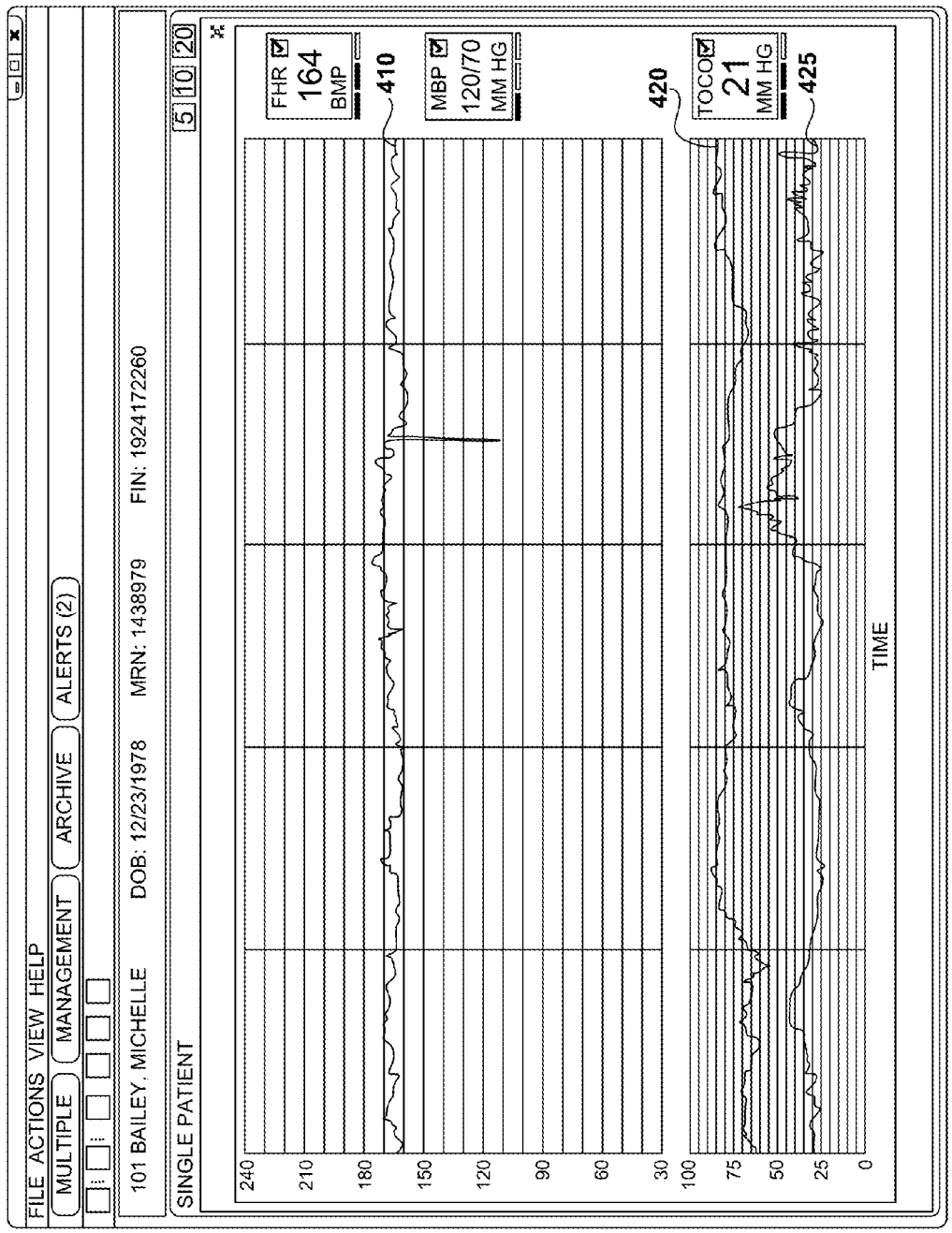
FIG. 5 is an illustrative screen display showing waveform tracings from one or more medical devices with at least one waveform disabled, in accordance with an embodiment of the present invention.

For example, with reference to FIGS. 4 and 5, a user has selected in FIG. 4 to hide the waveform 415 for maternal blood pressure as it interfering with fetal heart rate waveform 410 for which the clinician wants to see more clearly. The selection is received by receiving component 210 of FIG. 2. It is determined by a subcomponent of determining component 245 that waveform 415 is no longer to be displayed. Thus, in graphical user interface 500 of FIG. 5, waveform 415 is disabled and displaying component 250 displays the waveforms 410, 420 and 425 and not waveform 415.

Figure 6:
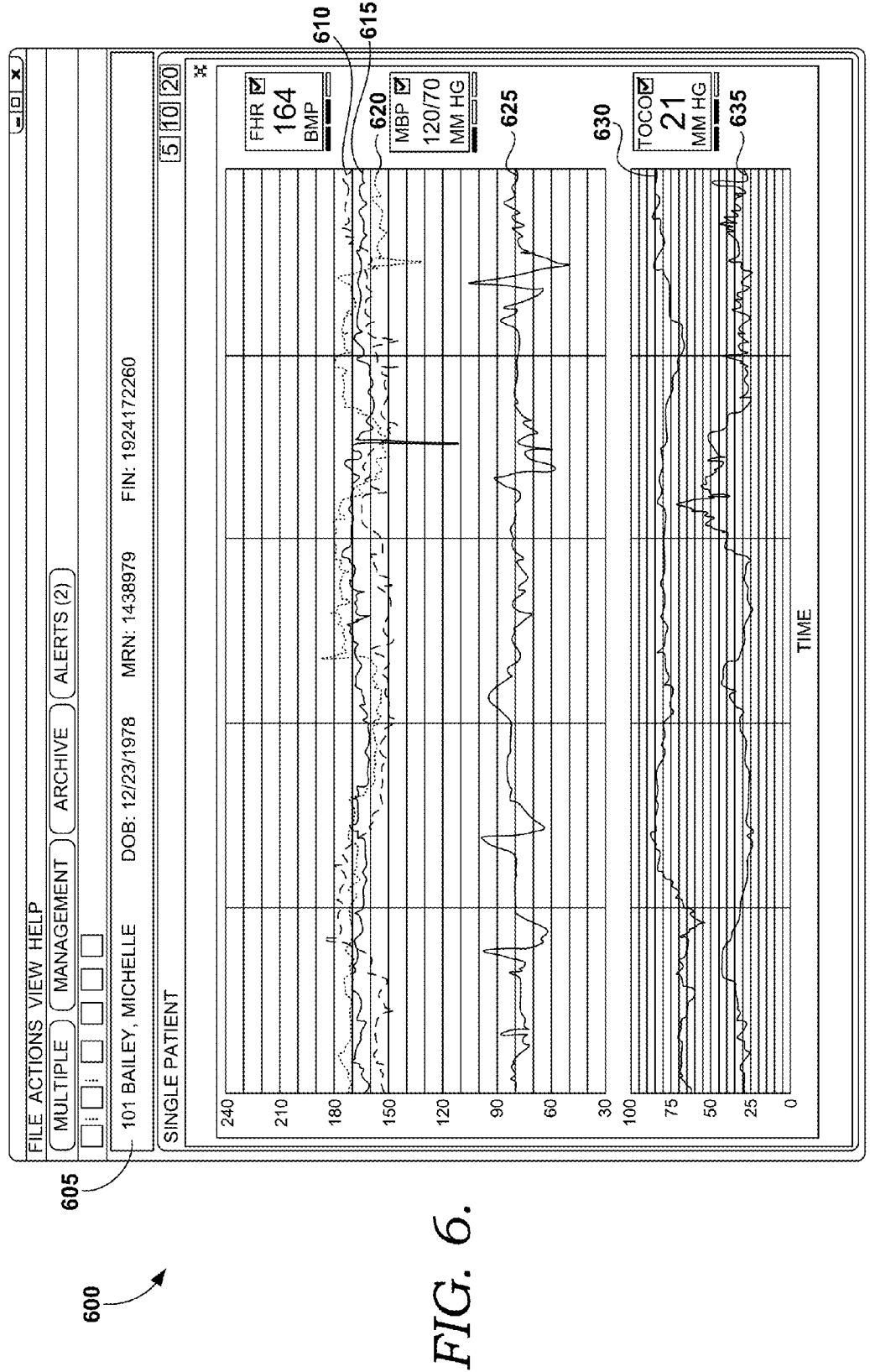
FIG. 6 is an illustrative screen display showing waveform tracings for multiple fetuses, in accordance with an embodiment of the present invention.
Figure 7:
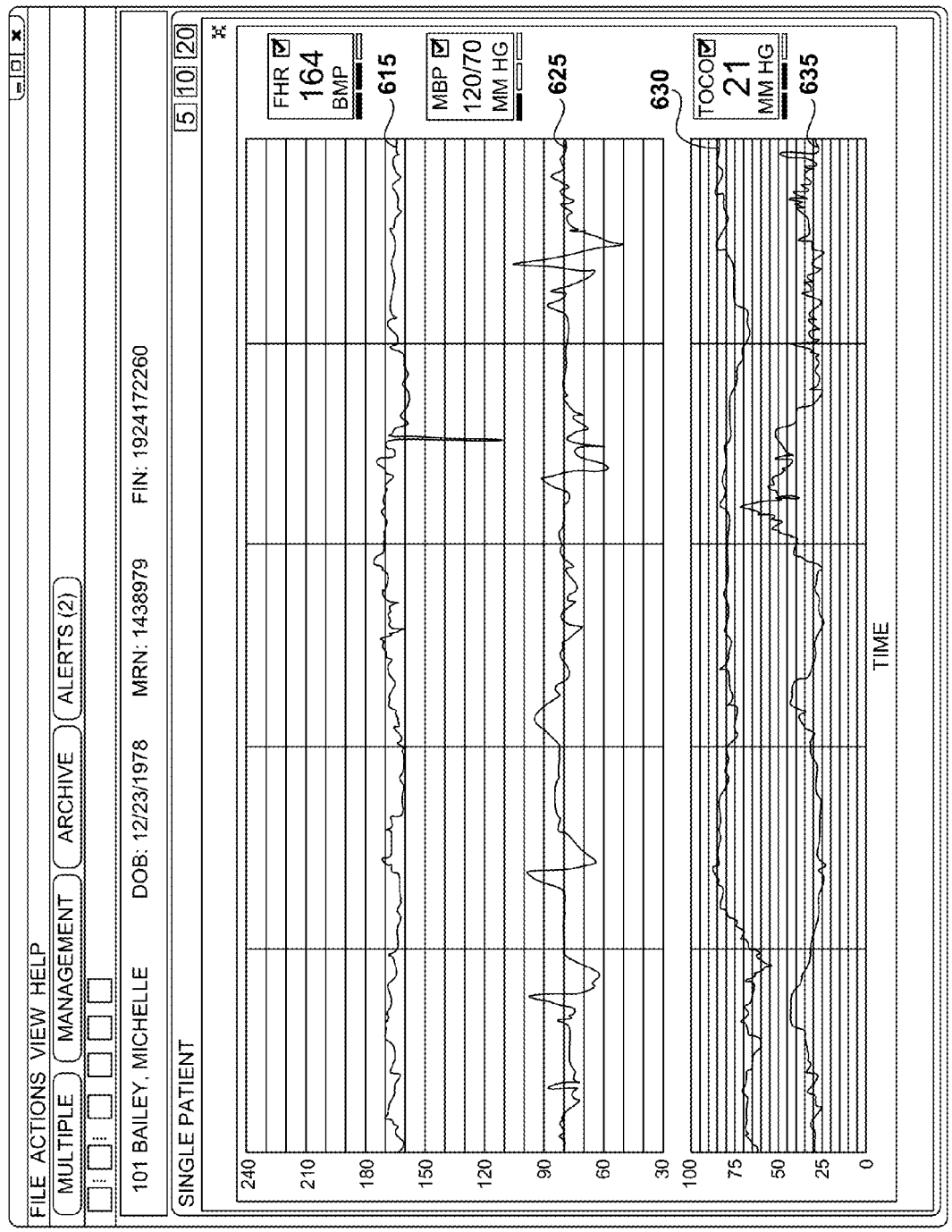
FIG. 7 is an illustrative screen display showing waveform tracings from one or more medical devices showing only one of multiple fetuses, in accordance with an embodiment of the present invention.

With reference to FIGS. 6 and 7, graphical user interfaces embodied on a computer-storage media displaying continuous data waveforms from one or more medical devices for two or more individuals is shown. Display 600 includes waveform tracings for a single maternity patient 605 and her unborn triplet babies 610, 615, and 620. In one example, if one of the multiples appears to be in distress, the clinician may choose to view only the waveform of the unborn baby in distress and hide the waveforms for one or more of the other unborn babies. The selection to hide one of the waveforms is received by receiving component 240 of FIG. 2. It is determined by determining component 245 that only waveform 615 is to be displayed. Thus, waveforms 610 and 620 are disabled and in graphical user interface display 700 of FIG. 7 displaying component 250 displays only waveform 615 and not waveforms 620 and 625.

Figure 8:
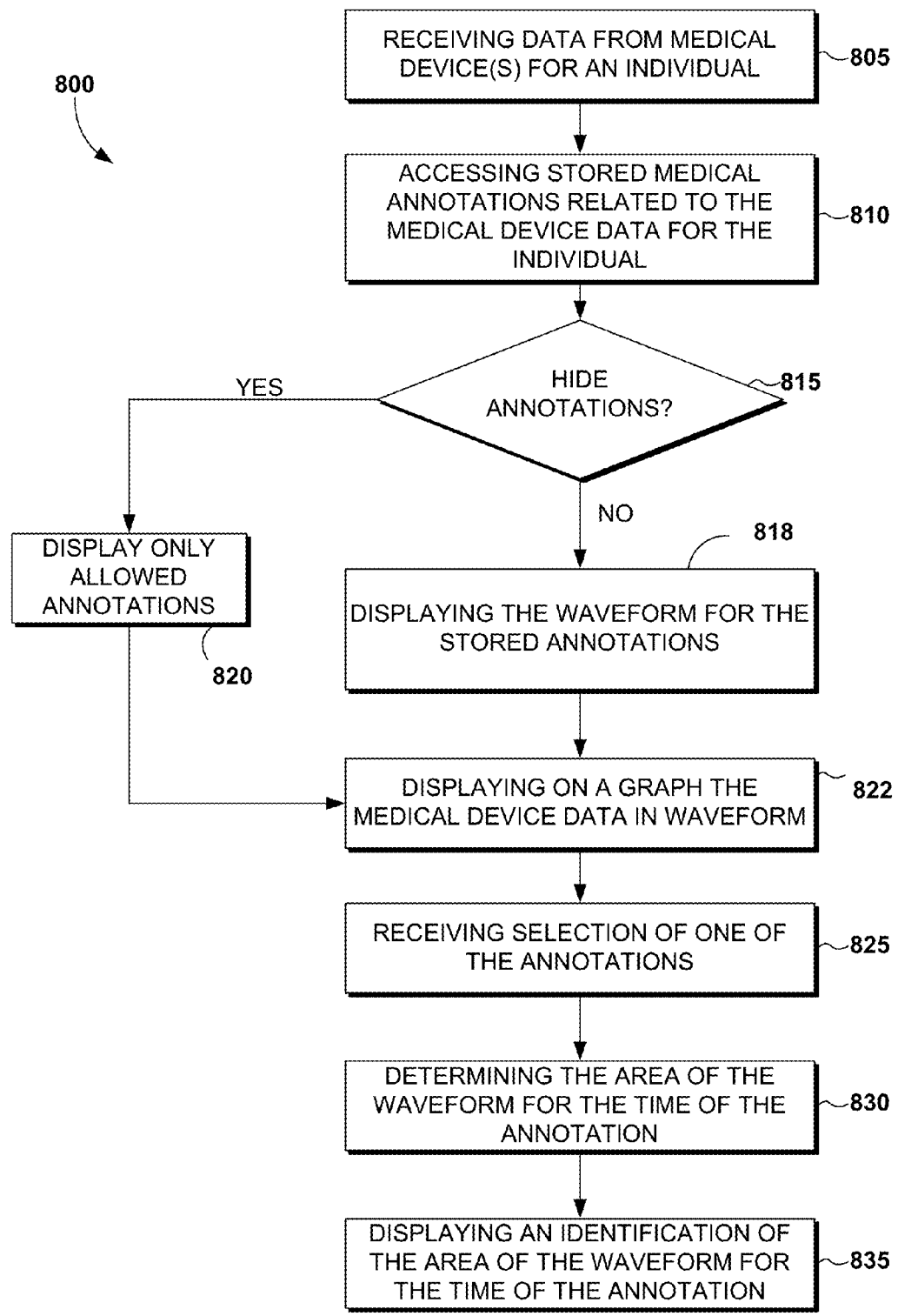
FIG. 8 is an illustrative flow diagram of a method for simultaneously displaying waveform tracings from one or more individuals and related medical annotations, in accordance with an embodiment of the present invention.

Referring next to FIG. 8, a computer-implemented method 800 for determining and displaying the area of a medical device waveform for an individual corresponding to the time of a textual annotation is shown. Computer-implemented method 800 is performed by one or more computer processors. At step 805, monitoring data from one or more medical devices for a first individual are received. In one embodiment, the first individual is a maternity patient. Exemplary monitoring data for the maternity patient includes heart rate data from a heart rate monitor, uterine pressure and contraction information from a uterine pressure and contraction activity monitor, blood oxygen saturation data from a blood oxygen saturation monitors and blood pressure from a blood pressure monitors.

At step 810, medical annotations related to the data received from the one or more medical devices is accessed and received. Medical annotations are accessed from database 215. The medical annotations may include textual notes, comments and observations by a clinician regarding are variety of things relating to the patient including the patient's condition, medical history, demographic information, test results and tasks and examinations performed for the patient. Common medical annotations utilized in labor and delivery may be displayed for selection by the clinician. In addition to accessing the medical annotations, any indication that one or more of the medical annotations should not be displayed is also accessed from database 215. The input of medical annotations is described below in more detail with reference to FIG. 9. At step 815, it is determined whether any of the annotations accessed from database 215 should be hidden. For example, a clinician may select to have certain annotations hidden at the time of entry or thereafter.

If it is determined that no annotations have been requested to be hidden at step 815, all related annotations are displayed at step 818. If it is determined that one or more annotations for the patient are to be hidden, at step 820, only annotations not identified to be hidden are displayed. At step 822, data from the medical devices for the first and second individuals is displayed as waveforms. As discussed above, the data from the medical devices is converted into electronic waveforms that can be displayed as tracings or graphs.

In one embodiment, at step 825, a user may select one or more of the annotations displayed at steps 820 and 822. The user may choose to view the related portion of a waveform tracing for the annotation by selecting or clicking on the annotation. At step 830, the associated area of one or more displayed waveforms is determined. For example, if an annotation was documented as occurring at 8:00 p.m., the area of one or more of the associated waveform for 8:00 p.m. for the individual is displayed. This may be done on a waveform with the most current data or in a separate waveform with historical data. In one embodiment, the current data waveform is displayed simultaneously with a historical data waveform for the individual and the area. This is described below in more detail with reference to FIG. 10.

Figure 9:
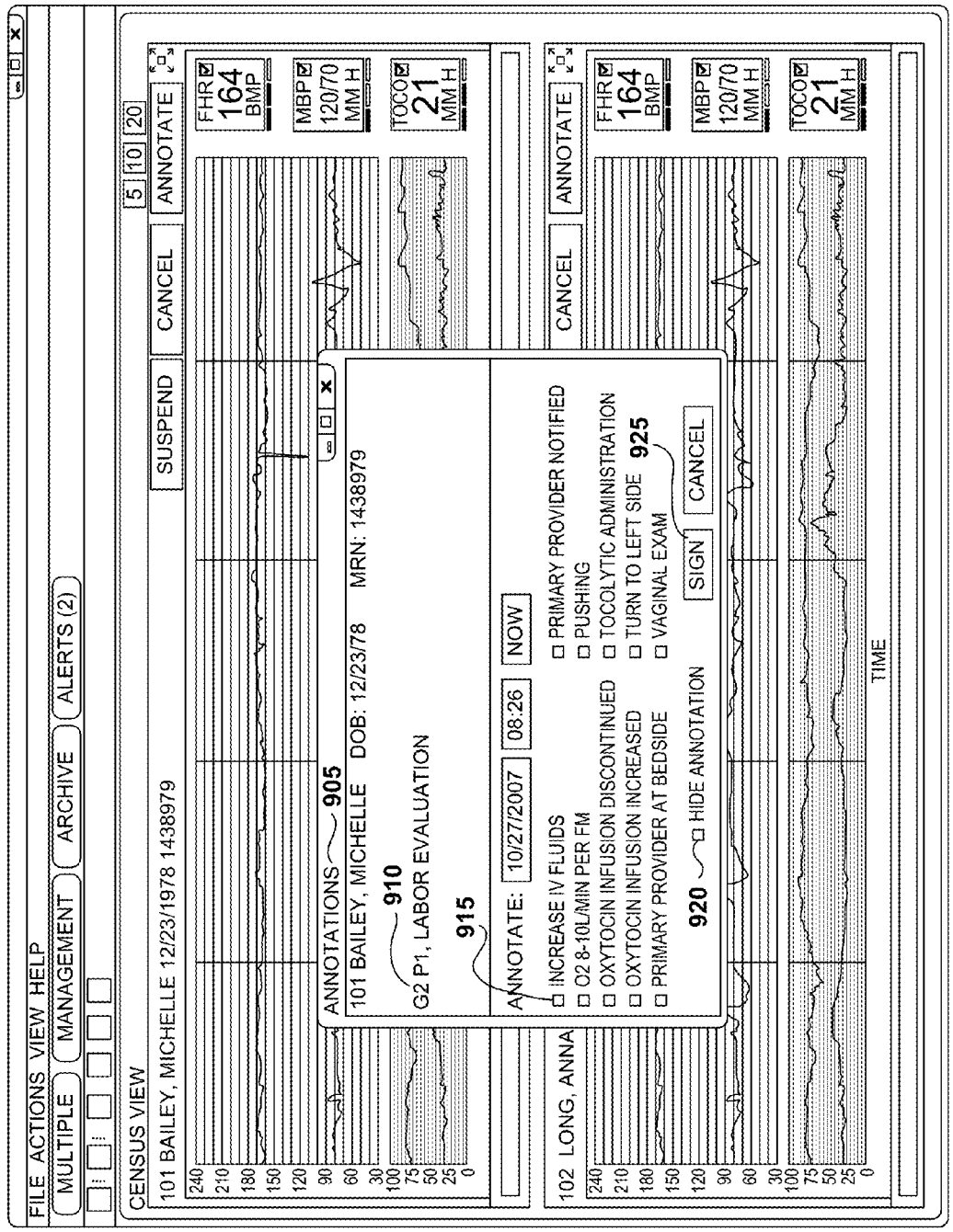
FIG. 9 is an illustrative screen display for allowing a user to input medical annotations for a labor and delivery patient, in accordance with an embodiment of the present invention.

As shown in FIG. 9, an exemplary graphical user interface 900 for allowing a user to input medical annotations for a labor and delivery patient is shown. As depicted in FIG. 9, the annotation box 905 is displayed along with waveform of medical device data for the maternity patient and unborn baby. Textual annotations may be input by a clinician into text box 910. Common medical annotations 915 for labor and delivery that may be selected by a clinician include, but are not limited to, increase IV fluids, O2 8-10 L/Min per FM, oxytocin infusion discontinued, oxytocin infusion increased, primary provider at bedside, primary provider notified, pushing, tocolytic administration, patient turned to left side and vaginal examination. The clinician may select sign button 925 to send and store any annotations made. The annotations along with the associated time and date when the annotation was made are then stored in database 215.

With regard to FIG. 9, a user, such as a nurse or doctor, may enter or select an annotation and choose to have it hidden for privacy reasons by selecting check box 1520. For example, sensitive information about the maternity patient, such as past pregnancies, terminated pregnancies, medical conditions (e.g., sexually transmitted diseases) and demographic information (e.g., weight) may be selected to be hidden by the clinicians so that non-medical personnel in the patient's room cannot see the annotations. Non-medical personnel may include persons in a non-medical care giving role such as family and friends of the patient and personnel of the healthcare facility that have no need to know the medical information contained in the annotation. This annotation and the selection to "hide" the annotation are stored in a database, such as database 215.

Figure 10:
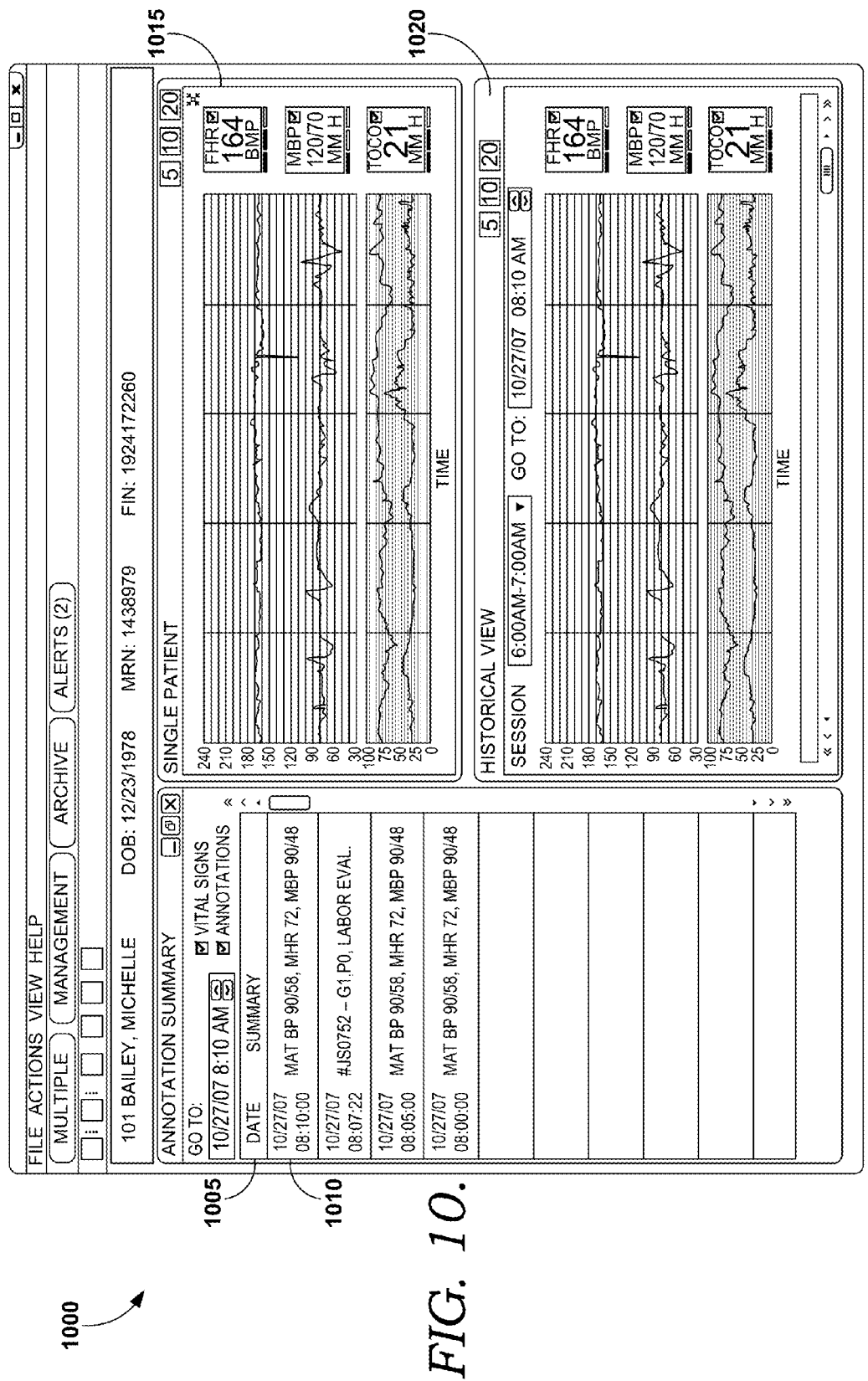
FIG. 10 is an illustrative screen display showing current and historical waveform tracings and textual annotations for a patient, in accordance with an embodiment of the present invention.

With reference to FIG. 10, an exemplary graphical user interface 1000 for displaying waveform data and related medical annotations for a patient is shown. As depicted in FIG. 10, medical annotations 1005 are in an area on the user interface 1000 separate from the display areas of current 1015 and historical 1020 waveform tracings for the patient. The current waveform tracing 1015 has the most recent data for the patient from one more medical devices. Historical waveform tracing 1020 has historical data for the patient from one or more medical devices for a specific time period. In this example, the exemplary specific historical time period for the patient is from 6 a.m. to 7 a.m. on Oct. 27, 2007. Medical annotations 1005 for the patient are listed from the most recent to the oldest. For example, medical annotation 1010 of maternal blood pressure and maternal heart rate is the most recent medical annotation for the patient.

Figure 11:
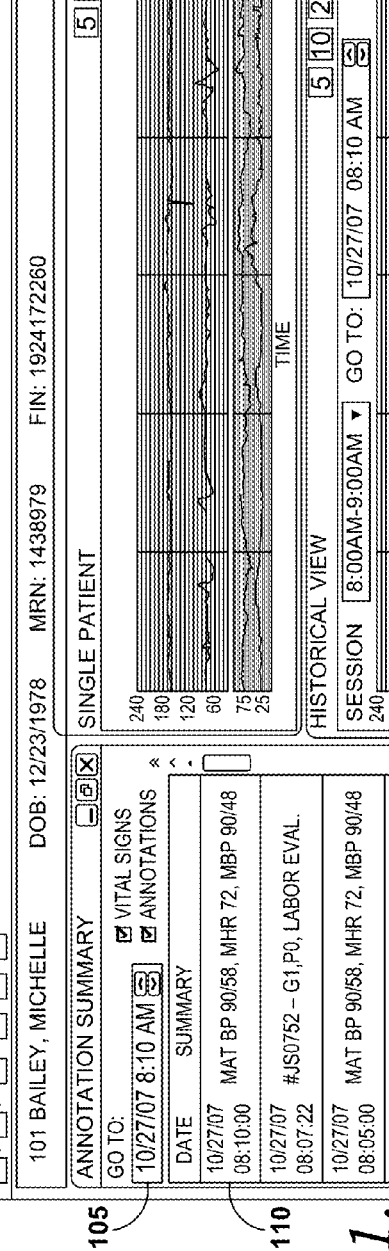
FIG. 11 is an illustrative screen display showing a portion of a waveform tracing related to a medical annotation, in accordance with an embodiment of the present invention.

Referring next to FIG. 11, an exemplary graphical user interface 1100 for displaying current, historical and archived waveform tracings along with medical annotations for a patient is shown. As depicted in FIG. 11, medical annotations 1105 are in an area on the user interface 1100 separate from the display areas of current 1120, historical 1125 and archived 1130 waveform tracings of data for the patient from one or more medical devices. The time frame on a waveform associated with a selected medical annotation is displayed. The current waveform tracing 1120 has the most recent data for the patient from one more medical devices on Oct. 27, 2007. Historical waveform tracing 1125 has historical data for the patient from one or more medical devices for a specific time period. In this example, the exemplary specific historical time period for the patient is from 6 a.m. to 7 a.m. on Oct. 27, 2007 which is an earlier time period of the same visit of the patient as the current 1120 waveform tracing. For example, the same visit of the patient may be an admission to a hospital or a doctor's visit. Archived waveform tracing 1130 is for a different visit of the patient on Oct. 13, 2007. In this example, the archive view includes annotations 1115 and waveform tracing 1130 for a previous hospital admittance or doctor's visit for the patient.

As described with reference to FIG. 8, a user may select one of the annotations 1110 and 1115 to view the related portion of the corresponding current 1120, historical 1125 or archived 1130 waveform tracing. For example, if annotation 1110 (made at 8:10 a.m. on Oct. 27, 2007) is selected by a user, the associated time period (8:00 to 9:00 a.m. on Oct. 27, 2007) on of the historical waveform tracing 1125 is displayed. An identification 1135 of the time corresponding to the time of the annotation (8:10 a.m. on Oct. 27, 2007) is displayed on waveform tracing 1125. If the user selects annotation 1115, the associated time period of the archived annotation is displayed on the archived waveform tracing 1130. An identification 1140 of the time corresponding annotation time is displayed on archived waveform tracing 1130.

Figure 12:
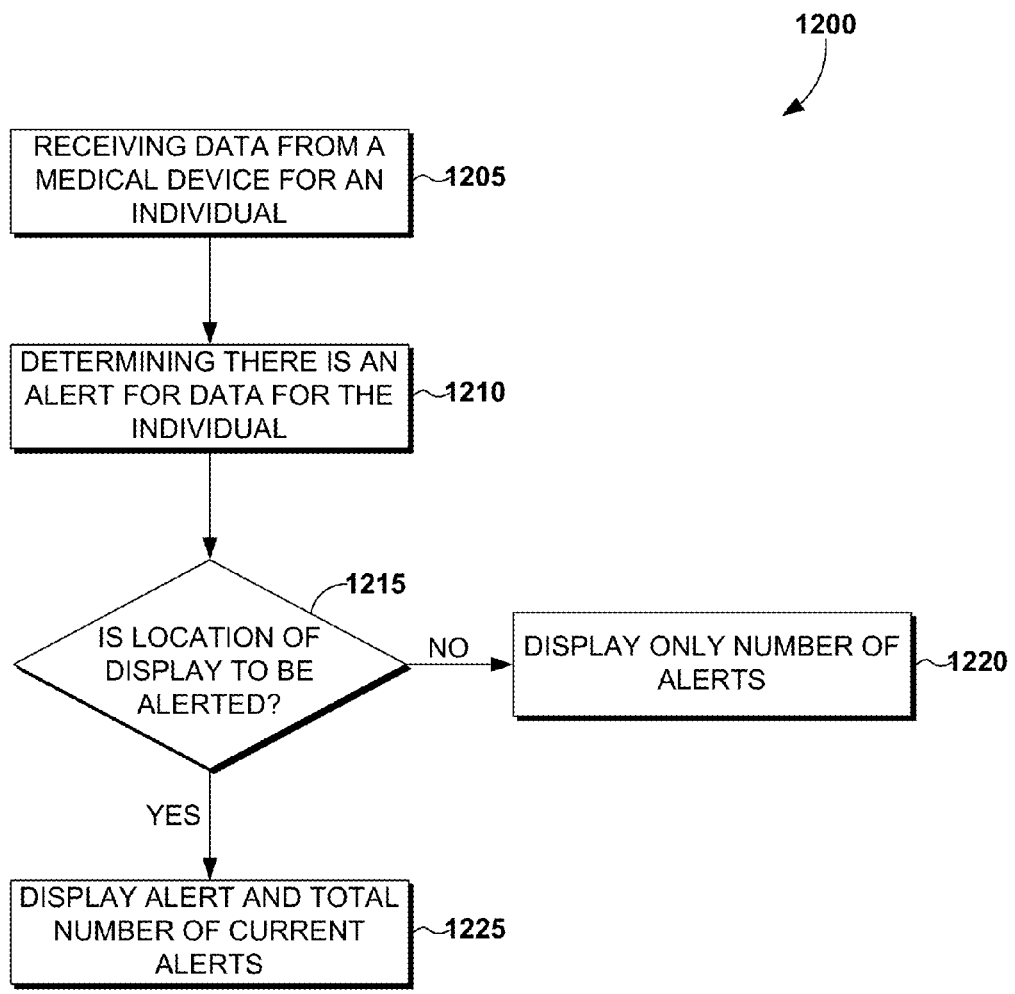
FIG. 12 is an illustrative flow diagram of a method for displaying alerts, in accordance with an embodiment of the present invention.

Referring next to FIG. 12, a computer-implemented method 1200 for displaying patient alert information based on location is shown. Computer-implemented method 1200 is executed by one or more computer processors. At step 1205, monitoring data from one or more medical devices for a patient is received. In one embodiment, the patient is a maternity patient or an unborn baby. Exemplary monitoring data is described above.

At step 1210, it is determined that the monitoring data received satisfies a rule that would trigger an alert. Exemplary rules include determining data for a heart rate is outside of a specified range, a patient's blood pressure outside of a specified range, uterine pressure and contraction data outside of a specified range, blood oxygen levels outside of a specified range and other data outside of a specified range. At step 1215, it is determined whether the location of the device displaying patient information is to be alerted. The determination is based on the physical location of the device and is not dependent on which user is logged on or signed into the device. In some instances, based on location of the device, all alerts for all patients are to be displayed. For example, a nurse manager may want to see all alerts for all patients. In some instances, based on the location of the display device, all alerts for only some patients are to be displayed. For example, if a floor is divided into multiple nursing units, each nursing unit including four patient rooms, only alerts for the patients in the patient rooms of the nursing unit will be displayed on devices located in the nursing unit. In some instances, based on the location of the display device, no alerts are to be displayed and only the number of alerts is to be displayed. For example, as the caregivers in the operating or c-section room cannot leave to respond to any alerts, an operating or c-section room may be designated as a location to display only the number of alerts and not the actual alert information.

At step 1220, if it is determined the display device location is not to display the content of the alerts; only the number of alerts is displayed. Alternatively, no information is displayed. At step 1225, if it is determined that the display device location is to display the alerts and alert content, the alert, alert content and total number of current alerts are displayed. In one embodiment, the alert and alert content are displayed at the display device location.

Figure 13:
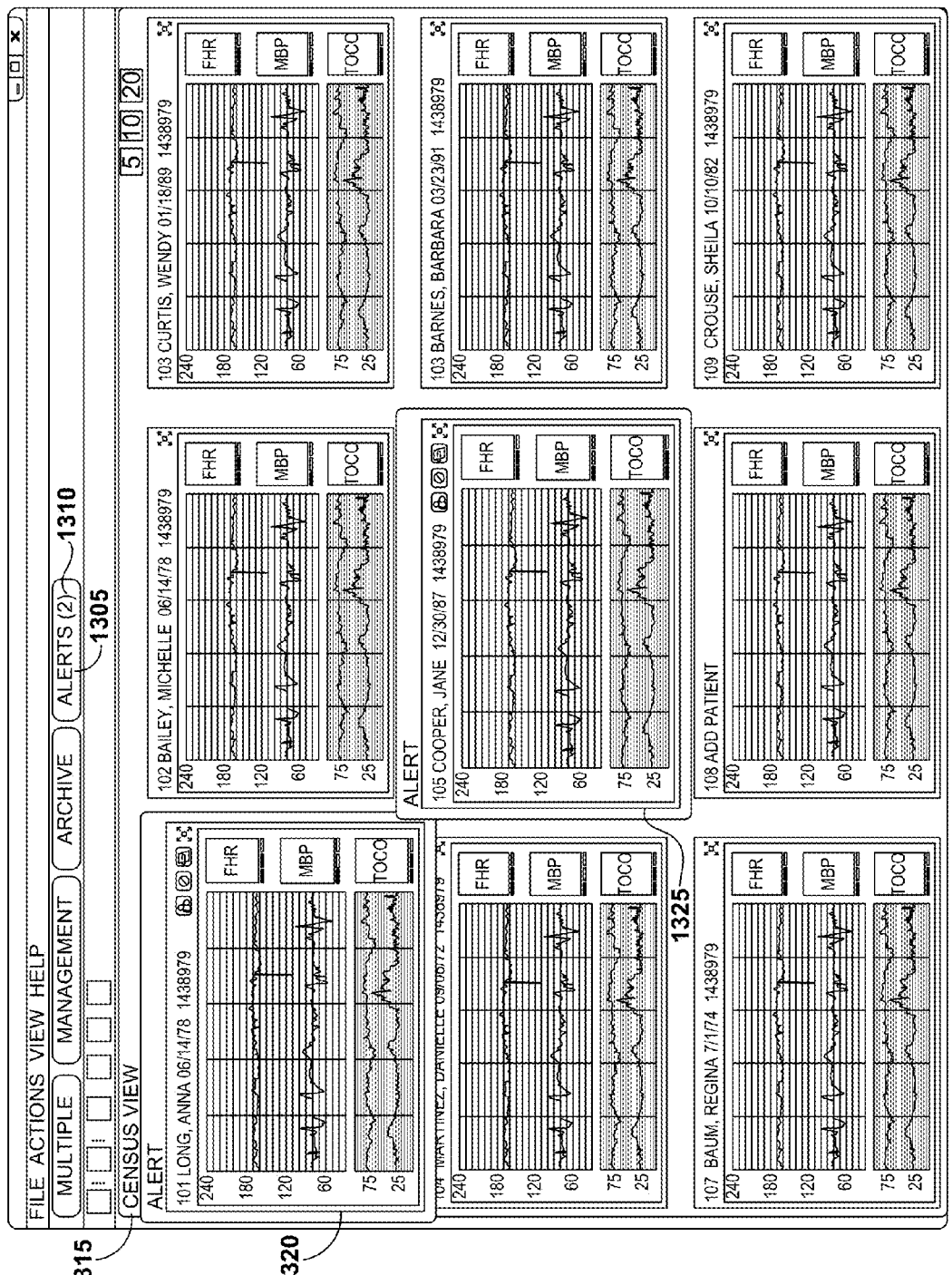
FIG. 13 is an illustrative screen display showing alerts and waveform tracings for multiple maternity patients, in accordance with an embodiment of the present invention.

Referring next to FIG. 13, an exemplary graphical user interface 1300 displaying waveform tracings of monitored data for multiple maternity patients 1315. Based on the location of the display device being utilized to display graphical user interface 1300, all alerts for all patients are displayed. It can be seen in exemplary graphical user interface 1300 that exemplary patients Anna Long 1320 and Jane Cooper 1325 are highlighted and are in alert. In addition, the total number of alerts 1305 is displayed on the graphical user interface so that a user can see how many alerts there are and identify necessary personnel to address the alerts. In this example, there are a total of two (2) 1310 patients in alert. A user may choose to view only waveform tracings for those patients with alerts. In one embodiment, this is done by selecting alert button 1305.

Figure 14:
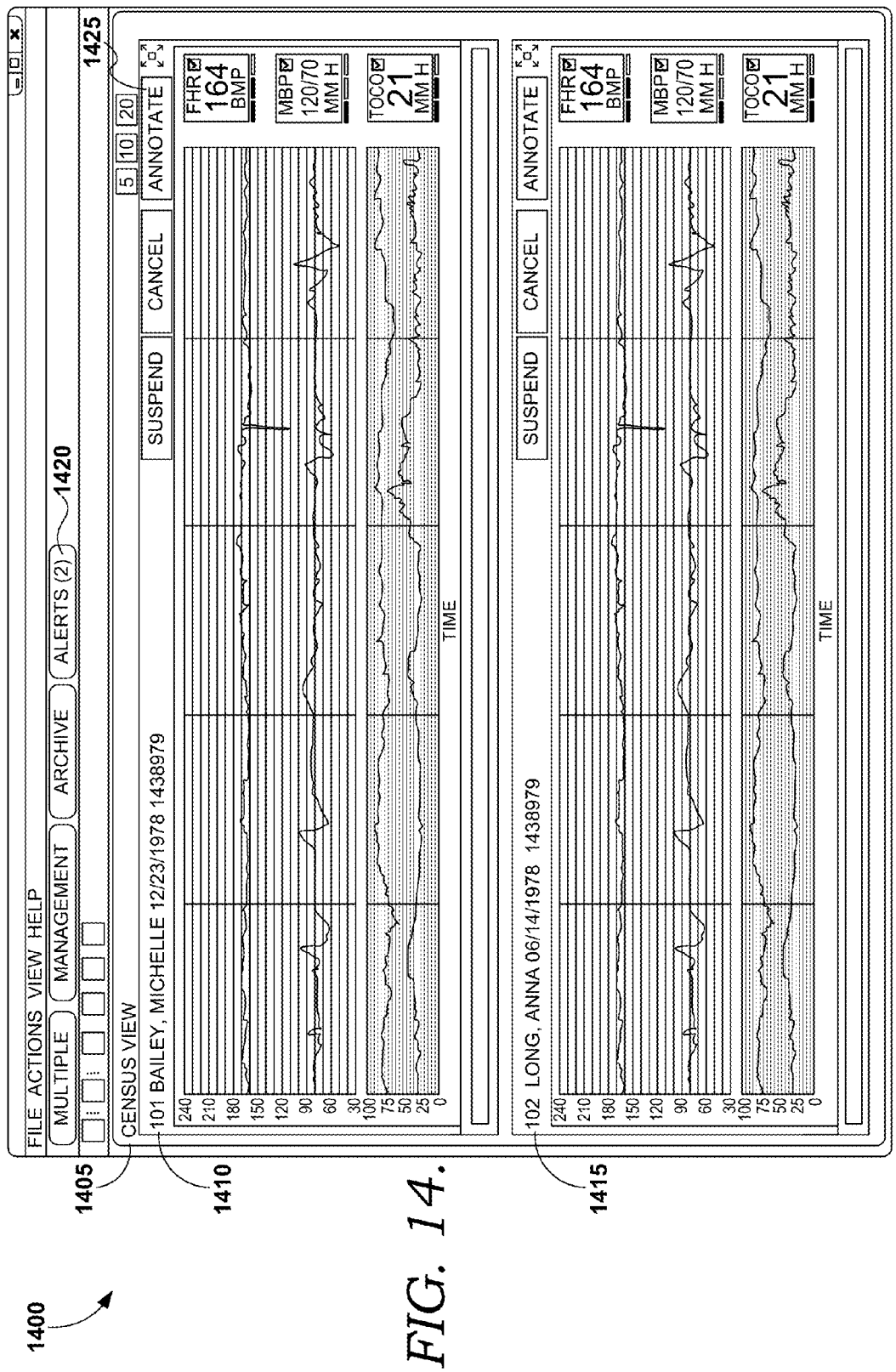
FIG. 14 is an illustrative screen display showing waveform tracings for maternity patients satisfying alert conditions, in accordance with an embodiment of the present invention.

Referring next to FIG. 14, an exemplary graphical user interface 1400 displaying waveform tracings for patients with alerts 1425 is shown. Graphical user interface 1400 includes the waveform tracings for fictitious patient Michelle Bailey 1410 and Anna Long 1415. A user may select to suspend, cancel and/or enter a textual annotation 1425 for the patient regarding the alert from graphical user interface 1400. The total number patients with alerts 1420 is displayed on the graphical user interface.

Figure 15:
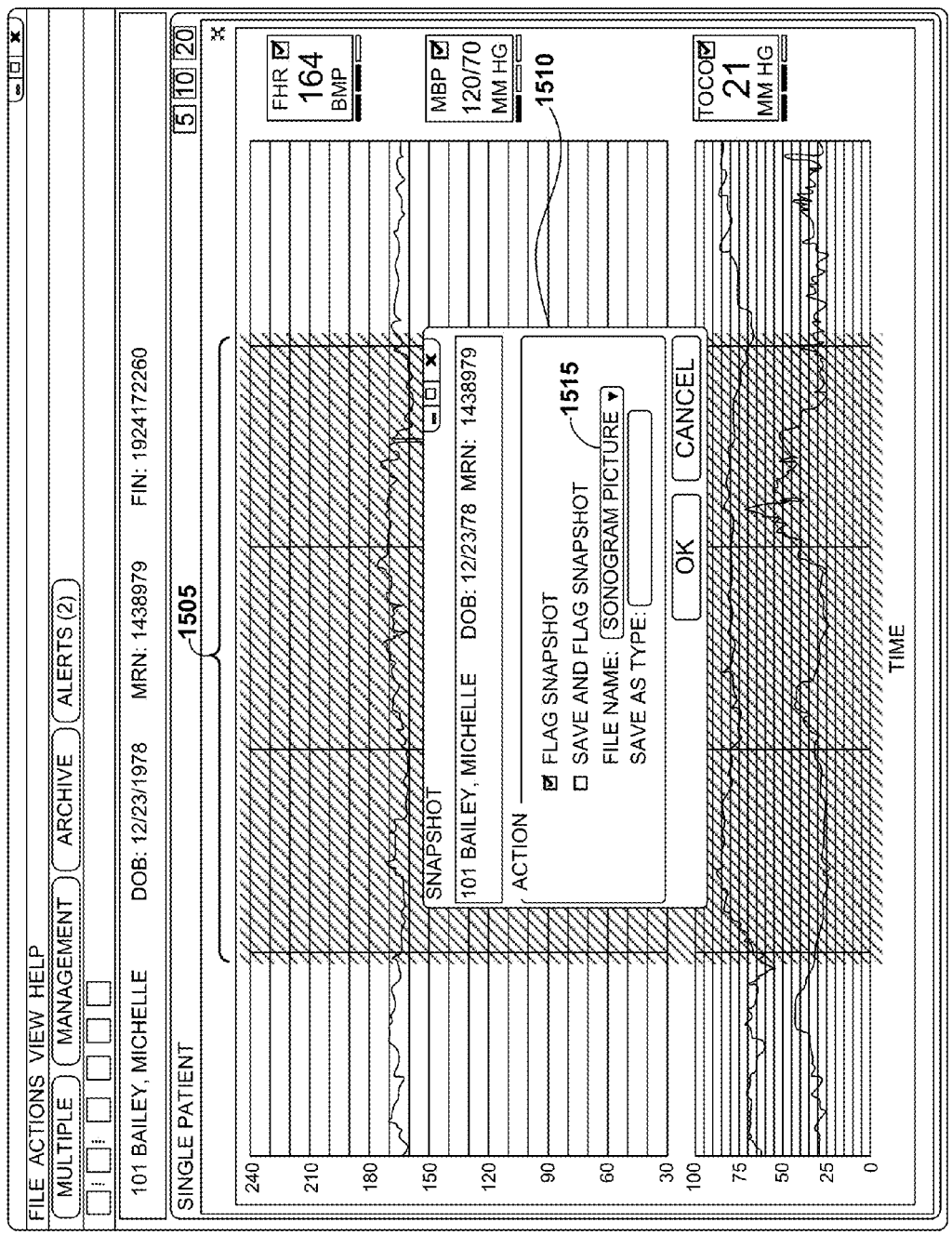
FIG. 15 is an illustrative screen display showing the identification of a portion of the waveform tracing for a patient being monitored, in accordance with an embodiment of the present invention.

FIG. 15 is an exemplary graphical user interface 1500 allowing a user to flag and store a portion of a waveform tracing 1505. Graphical user interface 1500 includes multiple waveform tracings for fictitious patient Michelle Bailey. A user, such as a nurse or clinician, flags a portion of the waveform tracing 1505. The user may then select to associate the portion of the waveform tracing 1505 with additional information for the patient such as textual entries, pictures, video, sonogram photographs, sonogram video, laboratory results and other stored files for the patient that relate to the time period of the waveform tracing 1505. For example, the portion of the waveform tracing 1505 may be for the period while a sonogram was being performed for the patient.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. Non-transitory computer storage media having computer-executable instructions embodied thereon that, when executed, cause a computing device to perform a method of displaying waveform tracings for data received from one or more medical devices, the method comprising:
  receiving a first set of medical annotations at a time, t, the
    first set of medical annotations comprising user-inputted
    textual notes, comments, and observations related to one
    or more of a first individual's demographic information, medical condition, or status, wherein the time, t, corresponds to a first hospital admittance or doctor's visit for the first individual;

receiving an indication that a first medical annotation of the first set of medical annotations be hidden;

storing the first set of medical annotations in a database including storing the indication that the first medical annotation be hidden;

receiving a first set of data from a medical device for the first individual at the time, t, the medical device monitoring the first individual for one of maternal uterine activity or maternal heart rate activity at the time, t;

storing the first set of data from the medical device in the database;

receiving a second set of data from the medical device for the first individual at a current time, $t_1$, the medical device monitoring the first individual for one of maternal uterine activity or maternal heart rate activity at the current time, $t_1$, wherein the current time, $t_1$, corresponds to a second hospital admittance or doctor's visit for the first individual, the second hospital admittance or doctor's visit occurring at a different date and time than the first hospital admittance or doctor's visit;

converting the second set of data into a first waveform tracing;

accessing from the database the first set of medical annotations database including the indication that the first medical annotation be hidden;

displaying, except for the first medical annotation, on a user interface the user-inputted textual notes, comments, and observations comprising the first set of medical annotations simultaneously with the first waveform tracing;

subsequent to displaying, except for the first medical annotation, on the user interface the user-inputted textual notes, comments and observations comprising the first set of medical annotations simultaneously with the first waveform tracing, receiving a user selection of a second medical annotation of the first set of medical annotations;

accessing from the database the first set of data and converting the first set of data into a second waveform tracing; and while continuing to display, except for the first medical annotation, the first set of medical annotations and the first waveform tracing, displaying on the user interface the second waveform tracing, wherein the second waveform tracing includes an indication of the time, t, at which the first set of data from the medical device was received.

2. The media of claim 1, further comprising:
subsequently receiving a user input to hide at least the first waveform tracing or the second waveform tracing; and
in response to receiving the subsequent user input, hiding the at least the first waveform tracing or the second waveform tracing.

3. The media of claim 1, further comprising:
displaying additional waveform tracings for the first individual.

4. The media of claim 1, wherein the first individual is a maternity patient.

5. The media of claim 4, further comprising:
while displaying the first and second waveform tracings on the user interface, displaying a third waveform tracing on the user interface, the third waveform tracing corresponding to a third set of data received from one or more medical devices for a second individual, wherein the second individual is an unborn baby of the maternity patient, and wherein the one or more medical devices monitor the second individual for one of fetal blood oxygenation saturation levels or fetal heart rate for the unborn baby.

6. The media of claim 5, further comprising:
displaying additional waveform tracings for the second individual.

* * * * *